US006274611B1

(12) United States Patent
Critchfield et al.

(10) Patent No.: US 6,274,611 B1
(45) Date of Patent: Aug. 14, 2001

(54) METHODS AND COMPOSITIONS FOR INHIBITION OF VIRAL REPLICATION

(75) Inventors: James W. Critchfield, Napa, CA (US); Thomas M. Folks, Lithonia; Salvatore T. Butera, Stockbridge, both of GA (US); John Coligan, Potomac, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/232,158

(22) Filed: Jan. 15, 1999

Related U.S. Application Data

(60) Provisional application No. 60/071,705, filed on Jan. 16, 1998.

(51) Int. Cl.$^7$ ............... A61K 31/415; A61K 31/525; A61K 31/38
(52) U.S. Cl. ............... 514/387; 514/251; 514/443
(58) Field of Search .................... 514/387, 251, 514/443

(56) References Cited

U.S. PATENT DOCUMENTS

| | | | |
|---|---|---|---|
| H1168 | 4/1993 | McKenna et al. | 514/28 |
| 5,061,715 | 10/1991 | Sunkara et al. | 514/314 |
| 5,063,238 | 11/1991 | Sunkara et al. | 514/340 |
| 5,256,534 | 10/1993 | Butera et al. | 435/5 |
| 5,444,085 | 8/1995 | Connor et al. | 514/443 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 | 9/1996 | Heath, Jr. et al. | 514/183 |
| 5,565,448 | 10/1996 | Nambi et al. | 514/215 |
| 5,612,330 | 3/1997 | Connor et al. | 514/211 |

OTHER PUBLICATIONS

Braddock et al, 114 CA:200619t, 1991.*
Ono et al, 113CA:163g, 1990.*
Berque, 118CA:94310, 1995.*
Ogawara et al, 111CA:19930, 1989.*
Zandomeni 111CA:169940, 1989.*
Butera, et al., "Compounds that Target Novel Cellular Components Involved in HIV–1 Transcription," *Mol. Med.*, vol. 1, No. 7, pp. 758–767 (1995).
Butera, et al., "Oscillation of the Human Immunodeficiency Virus Surface Receptor is Regulated by the State of Viral Activation in a CD4+ Cell Model of Chronic Infection," *J. of Virol.*, vol. 65, No. 9, pp. 4645–4653 (1991).
Critchfield, et al., "Casein Kinase II is a Selective Target of HIV–1 Transcriptional Inhibitors," *Proc. Natl. Acad. Sci. USA*, vol. 94, pp. 6110–6115 (1997).
Critchfield, et al., "Inhibition of HIV Activation in Latently Infected Cells by Flavonoid Compounds," *AIDS Research and Human Retroviruses*, vol. 12, No. 1, pp. 39–46 (1996).

Folks, et al., "Biological and Biochemical Characterization of a Cloned LEU–3 Cell Surviving Infection with the Acquired Immune Deficiency Syndrome Retrovirus," *J. Exp. Med.*, vol. 164, pp. 280–290 (1986).
Ghenbot, et al., "Purification of Liver Aldehyde Dehydrogenase by p–Hydroxyacetophenone–Sepharose Affinity Matrix and the Coelution of Chloramphenicol Acetyl Transferase from the Same Matrix with Recombinantly Expressed Alehyde Dehydrogenase," *Prot. Exp. and Purif.*, vol. 3, pp. 370–378 (1992).
Lori, et al., "Hydroxyurea as an Inhibitor of Human Immunodeficiency Virus–Type 1 Replication," *Science*, vol. 266, pp. 801–805 (1994).
Luscher, et al., "Biosynthesis of Casein Kinase II in Lymphoid Cell Lines," *Eur. J. Biochem.*, vol. 220, pp. 521–526 (1994).
Marshak, et al., "Synthetic Peptide Substrates for Casein Kinase II," Methods in Enzymology, vol. 200, pp. 134–156 (1991).
McElhinny, et al., "Casein Kinase II Phosphorylates IκBα at S–283, S–289, S–293, and T–291, and Is Required for Its Degradation," *Mol. and Cell, Biol.*, vol. 16, No. 3, pp. 899–906 (1996).
Schubert, et al., "Differential Activities of the Hyman Immunodeficienty Virus Type 1–Encoded Vpu Protein are Regulated by Phosphorylation and Occur in Different Cellular Compartments," *J. of Virol.*, vol. 68, No. 4, pp. 226–2271 (1994).
Schubert, et al., "Human–immunodeficiency–virus–type–1–encoded Vpu Protein is Phosphorylated by Casein Kinase II," *Eur. J. Biochem.*, vol. 204, pp. 875–883 (1992).
Schubert, et al., "The Human Immunodeficiency Virus Type 1 Encoded Vpu Protein is Phosphorylated by Casein Kinase–2 (CD–2) at Positions Ser52 and Ser56 within a Predicted α–Helix–Turn–α–Helix–Motif," *J. Mol. Biol.*, vol. 236, pp. 16–25 (1994).
Shugar, "Development of Inhibitors of Protein Kinases CK1 and CKII and Some Related Aspects, Including Donor and Acceptor Specificities and Viral Protein Kinases," *Cell. and Mol. Biol. Res.*, vol. 40, Nos. 5/6, pp. 411–419 (1994).
Sutton, et al., "Identification of Myocardial Protein from Two–Dimensional Gels by Peptide Mass Fingerprinting," *Electrophoresis*, vol. 16, pp. 308–316 (1995).
Vincent, et al., "The Human Immunodeficiency Virus Type 1 Vpu Protein: A Potential Regulator of Proteolysis and Protein Transport in the Mammalian Secretory Pathway," *Virology*, vol. 213, pp. 639–649 (1995).

* cited by examiner

Primary Examiner—Russell Travers
(74) Attorney, Agent, or Firm—Needle & Rosenberg

(57) ABSTRACT

The present invention comprises methods and compositions for treating viral infection by inhibiting the activity of host cellular enzymes. More specifically, methods and compositions comprising casein kinase II inhibitors and various related compounds such as precursors, analogs, metabolites and hydrolysis products that inhibit cellular proteins and thus viral replication are provided.

8 Claims, 2 Drawing Sheets

METHODS AND COMPOSITIONS FOR INHIBITION OF VIRAL REPLICATION

RELATED APPLICATIONS

This application claims priority to U.S. Provisional Patent Application No. 60/071,705, filed Jan. 16, 1998, herein incorporated in its entirety.

This invention was made by the Centers for Disease Control, an agency of the United States Government. The United States Government has certain rights in this invention.

TECHNICAL FIELD

The present invention relates to methods and compositions for treating diseases by inhibiting the activity of cellular enzymes. More particularly, the present invention relates to methods and compositions for treating viral infections by inhibiting cellular enzymes such as casein kinase II.

BACKGROUND OF THE INVENTION

One of the greatest challenges to modern medicine is the treatment of viral infections. Though there are therapies that are somewhat effective against viruses, most of the present treatments have multiple adverse side effects. In recent years, the research into treatment of viral diseases has been spurred by the emergence and rapid spread of viruses, particularly retroviruses, and very particularly Human Immunodeficiency Virus (HIV), that causes acquired immunodeficiency syndrome(AIDS).

The retroviridae comprise a large family of viruses, primarily associated with vertebrates, although there have been a few reported sightings in other animals. Both in the wild and in the laboratory, the retroviridae are associated with many diseases, including rapid and long-latency malignancies, wasting disease, neurological disorders and immunodeficiencies, as well as lifelong viremia in the absence of any obvious ill effects. Despite the variety of interactions with the host, all retrovirus isolates are quite similar in virion structure, genome organization, and mode of replication.

Retroviruses are a class of ribonucleic acid (RNA) viruses that replicate by using reverse transcriptase to form a strand of complementary DNA (cDNA) from which a double stranded, proviral DNA is produced. This proviral DNA is then incorporated into the chromosomal DNA of the host cell, thereby making possible viral replication by later translation of the integrated DNA containing the viral genome. Thus, all progeny cells of the originally infected host cell will contain the retroviral DNA. In addition, when multiple copies of the infectious virus are produced, other cells become infected.

Retroviruses cause both malignant and nonmalignant diseases. Expression of the viral genes of some retroviruses may be oncogenic, or may have other pathologic effects that alter normal cell function or produce cell death. The same virus may cause different diseases in different animals. For example, bovine leukemia virus causes B cell lymphoma in cows, T cell lymphoma in sheep, and immunodeficiency disorder similar to AIDS in rabbits and subhuman primates. The first two human retroviruses discovered were human T cell leukemia virus I and II (HTLV-I and II). HTLV-I was found to cause leukemia in humans. The third such human virus to be discovered, HTLV-III, now referred to as HIV, was found to cause cell death after infection of T-lymphocytes, specifically the CD4 subpopulation. HIV has been identified as the causative agent of acquired immune deficiency syndrome (AIDS) and AIDS related complex (ARC).

In addition to the usual viral capsid, retroviruses have an outer membrane of lipid and glycoprotein, similar to the membrane of ordinary cells. Indeed the lipid of the retroviral membrane is derived directly from the membrane of a previously infected host cell, however, glycoproteins inserted into the viral membrane are unique to the virus itself and are coded for by the viral genome. Infection of a host cell by a retrovirus initially relies on the interaction of various receptors on the host cell surface with the glycoprotein membrane envelope of the virus. Subsequently the virus and cell membranes fuse, and the virion contents are released into the host cell cytoplasm.

The host cells predominantly attacked by HIV are the CD4 cells. Infection of human CD4 cells by HIV has been shown to involve binding of the HIV gpl20 surface glycoprotein to a receptor on the surface of the CD4+ cells, the CD4 molecule itself. Recently it has been observed that binding and fusion of HIV to CD4+ cells is also dependent on co-receptor molecules.

While there are many influences controlling the clinical progression from viral infection to disease, a critical factor in AIDS is the continued replication of HIV within target cells and tissues, especially late in the disease process. The balance between infected cells actively replicating HIV and those harboring the provirus in a dormant state, has not been fully elucidated during the clinically asymptomatic period. Therapeutic intervention to alter clinical progression to AIDS, especially during the asymptomatic period, is needed. It is important to control both active HIV replication, and inhibition of viral activation.

A unique aspect of HIV is the part of its life cycle which consists of the multistep transition from an integrated provirus to the production and release of new virions. This transition phase is known as the efferent phase. Agents that have been shown to initiate activation of this phase in vitro include tumor necrosis factor α (TNF-α), granulocyte-macrophage colony-stimulating factor (GM-CSF), interleukin 6 (IL-6), phorbol esters, heat shock, ultraviolet (UV) irradiation, and others.

The numerous individual steps that make up the efferent phase range from early signaling events at the cell membrane to the budding and release of nascent virions. One of the host cell proteins involved in this process is nuclear factor κB (NF-κB). NF-κB is an inducible transcription factor involved in the regulation of numerous genes. This heterodimeric protein is present in the cytosol as an inactive complex with its natural inhibitor, I-κB. A variety of activating stimuli result in the liberation and activation of NF-κB from I-κB. One theory of activation is that the subsequent translocation of NF-κB to the nucleus and its association with κB-binding elements in the HIV promotor are involved in HIV transcription.

In most resting cells, NF-κB is anchored in the cytoplasm by its association with inhibitory molecules known as IκKs. This family of ankyrin-containing inhibitors include IκBα, IκBβ, IκBγ, the p105 precursor of p50, and the p100 precursor of p52. The classic NF-κB complex consists of a heterodimer of p50 (NF-κB) and p65 (Rel A). These two subunits are members of a family of factors with homology to the c-rel proto-oncogene. In response to a variety of stimuli, combinations of these cytoplasmic c-rel-like factors translocate to the nucleus and transactivate specific target genes.

With the exception of the viral trans-activator Tat, HIV transcription is critically dependent upon host cell transcription machinery and NF-κB is an important host cell transcriptional protein for HIV activation. Antioxidants and other pharmacologic agents that block HIV promoter-directed gene expression may interfere with the dissociation of pre-formed NF-κB from its cytoplasmic inhibitor, I-κB.

Therapeutic Intervention

Although some antiviral treatments are presently available, additional attempts to design drugs for therapy of viral infections, particularly AIDS, are still necessary. Some therapies used to treat viral infectious, in particular HIV infections, are also used as chemotherapy agents.

During all stages of clinical progression to AIDS, HIV expression continues and may contribute to the cumulative destruction of the immune system. Alternative approaches to HIV-1 treatment currently being studied include (1) use of soluble forms of CD4 or co-receptor antagonists; (2) inhibition of glycosylation reactions necessary for attachment of sugar molecules to viral glycoproteins; (3) inhibition of HIV protease, an enzyme necessary to cleave functional proteins from large protein precursors; and (4) immunization of infected persons to boost their protective immunologic response.

Another treatment for AIDS is use of chemotherapeutic agents. Hydroxyurea for example, has been widely used over the last thirty years for the treatment of human malignancies, especially chronic myelogenous leukemia and other myeloproliferative syndromes. Hydroxyurea inhibits deoxynucleotide synthesis and consequently DNA synthesis by blocking the cellular enzyme ribonucleotide reductase. Hydroxyurea inhibits human immunodeficiency virus-type 1 (HIV-1) DNA synthesis in activated peripheral blood lymphocytes by decreasing the amount of intracellular deoxynucleotides. Combination of hydroxyurea with the nucleoside analogs ddC or ddI generates a synergistic inhibitory effect of HIV without increasing toxicity. In some instances, inhibition of HIV-1 by hydroxyurea is irreversible, even several weeks after suspension of drug treatment.

Therapeutic intervention in viral infections can occur (1) before or at the time of viral particle attachment to host cell membranes, (2) during uncoating of viral nucleic acids, (3) by inhibiting a cellular receptor or factor required for viral replication, or (4) by blocking specific virus-coded enzymes and proteins produced in the host cells that are essential for viral replication but not for normal host cell metabolism.

Difficulties with antiviral therapy arise because of the obligatory dependence of viruses on host cell metabolism for replication, and because of rapid mutations of virus-specific enzyme systems vulnerable to therapeutic intervention. Agents that block viral replication also block normal host cell processes, and the limits between effective and toxic doses are very narrow. Some clinically useful antiviral agents have a wide variety of side effects and a relatively low therapeutic index. In addition, patients receiving these agents must be monitored carefully, and resistant virus strains often develop in patients receiving initially effective therapy.

Another treatment for AIDS is Azidothymidine (AZT), also known as zidovudine. AZT is a dideoxynucleotide and is used widely as a treatment for viral infection. AZT and related compounds are potent inhibitors of replication of HIV in vitro. AZT is converted to its triphosphate form by cellular enzymes and then AZT exerts its antiviral activity at the reverse transcription level by interfering with viral DNA synthesis. Viral reverse transcriptase (RT) is an enzyme that is essential for the production of a DNA copy of the viral genome. AZT competes with cellular deoxynucleoside triphosphate substrates that are essential for the nascent formation of proviral DNA and act as a chain terminator for nascent DNA strands.

AZT has been shown to decrease viral replication and to result in an increase in CD4+ cell counts, at least transiently. Treatment with AZT results in longer survival of patients with AIDS, and has been shown to retard the onset of clinical disease in patients infected or minimally symptomatic from their HIV infection. AZT is not, however, a cure for HIV infection or its associated diseases. Usual toxicity associated with use of AZT relates to suppression of bone marrow cells, resulting in anemia, thrombocytopenia, and/or granulocytopenia. Other complications associated with the use of AZT include nausea and headaches. Despite their differences in structure, antiviral activity and pharmacokinetic properties, ddI, zidovudine (azidothymidine or AZT) noncompetitive HIV-1 reverse transcriptase inhibitors, and HIV-1 protease inhibitors share a common feature: they directly target viral proteins, and therefore, are subject to escape by viral mutations.

The serious need for an effective anti-HIV treatment increases daily. It is estimated that world-wide there are almost 23 million people infected with one or more of the ten known subtypes of HIV and that number grows by approximately 8500 persons each day. In the industrialized countries of the world, the average cost of therapy for a patient with HIV has risen to an estimated $12,000 to $16,000 per year. The new protease inhibitor combination therapies are expected to further increase the costs of treatment.

Thus, methods and compositions for the treatment of viral infections are needed that are capable of targeting one or more cellular components. Such a treatment would avoid triggering the onset of viral escape mutants as a result of direct selective pressure against viral proteins. Treatments are needed that achieve specific antiviral effects with a drug having little, or no, toxic effects on the cell.

SUMMARY OF THE INVENTION

In accordance with the present invention, compositions and methods are provided that are effective in inhibiting the activity of specific cellular components associated with viral replication, specifically protein kinase enzymes such as casein kinases. These compositions are easily administered by oral, subcutaneous and intravenous routes, and can be given in dosages that are safe, and provide inhibition of viral replication. The present invention provides a method of treating mammalian diseases mediated by viral infection by administering a composition comprising an anti-viral compound in a dosage sufficient to inhibit transcription and/or translation of viral genomes thereby preventing the propagation of viral particles. Such compounds include casein kinase II inhibitors and various related compounds such as precursors, analogs, metabolites and hydrolysis products.

The present invention is especially useful for treating viral diseases such as those caused by retroviruses including Human Immunodeficiency Virus (HIV). Other viral diseases that can be treated using the present invention include infection by RNA genome viruses, particularly vesicular stomatitis virus, respiratory syncitial virus, and measles virus.

Accordingly, it is an object of the present invention to provide compositions and methods to treat viral infections in a human or animal.

Another object of the present invention is to provide a composition for inhibiting viral replication by oral, subcutaneous, or intravenous administration of the composition.

It is a further object of the present invention to provide a treatment for diseases mediated by viral infection.

It is yet another object of the present invention to provide a treatment for AIDS.

Another object of the present invention to provide a treatment for all types of retroviral infections including those types not associated with AIDS.

It is a further object of the present invention to provide compositions and methods for treatment of diseases caused by infections of vesicular stomatitis virus.

It is yet another object of the present invention is to provide methods and compositions for the treatment of diseases caused by infections of respiratory syncitial virus.

It is yet another object of the present invention to provide methods and compositions for the treatment of diseases caused by infections of measles virus.

These and other objects, features and advantages of the present invention will become apparent after a review of the following detailed description of the disclosed embodiments and the appended claims.

DETAILED DESCRIPTION

Figure 1:
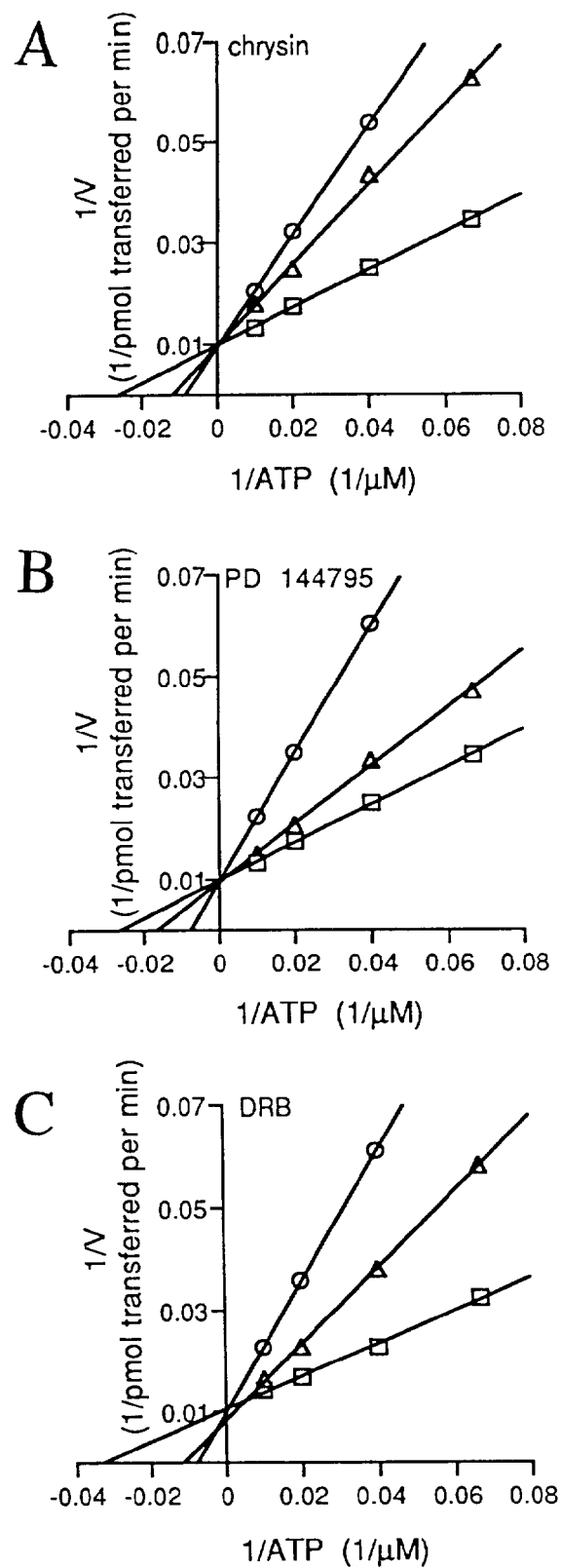
FIG. 1(A) is a graph showing the kinetics of inhibition of CKII enzyme activity by chrysin (—☆—, 10 $\mu$M; —△—, 3 $\mu$M; —□—, 0 $\mu$M).
FIG. 1(B) is a graph showing the kinetics of inhibition of CKII enzyme activity by PD 144795 (a benzothiophene) (—☆—, 10 $\mu$M; —△—, 3 $\mu$M; —□—, 0 $\mu$M).
FIG. 1(C) is a graph showing the kinetics of inhibition of CKII enzyme activity by 5,6-dichloro-1-$\beta$-D-ribofuranosylbenzimidazole (DRB) (—☆—, 50 $\mu$M; —△—, 25 $\mu$M; —□—, 0 $\mu$M).

Compositions and methods for the treatment of viral disease that are mediated by inhibition of viral replication are provided. Particularly, methods and compositions of the present invention are directed to inhibition of protein kinase enzymes such as casein kinase II in mammalian cells. Inhibition of protein kinases inhibits the replication, including transcription and translation, of many types of viruses. Among other activities, such inhibition leads to the inability of the cell to support the replication of viruses including HIV-1 (Human Immunodeficiency Virus-1). Such compounds include casein kinase II inhibitors and various related compounds such as precursors, analogs, metabolites and hydrolysis products.

Inhibition of Viral Transcription and Replication

The identification of cellular factors that are required to complete various steps of a virus lifecycle is important for the development of new therapeutics. Herein, the lifecycle of HIV-1 is discussed, though it is intended as an example. The present invention is not limited to treatments for retroviral infections, but is also intended for treatments for other viruses, particularly RNA genome viruses.

One key step of the viral replication process for retroviruses, transcription from the integrated provirus, is inhibited by members of two structurally distinct classes of compounds, the flavonoids and the benzothiophenes. A marked specificity of these compounds toward inhibiting HIV-1 transcription, is evidenced by the ability of drug-treated cells to retain their proliferative and differentiation capabilities. In addition, flavonoids and benzothiophenes do not impede the activation and function of the transcriptional factor NF-κB. Chemical and immunologic analyses disclosed herein have identified the cellular factors targeted by the flavonoids and the benzothiophenes as the individual subunits of casein kinase II (CKII). Thus, the benzothiophenes and flavonoids specifically inhibit CKII, without interfering with cellular transcription factors such as NF-κB, and yield selective inhibition of HIV.

It is the inventor's surprising finding that selective inhibition of CKII by compositions, such as the benzothiophenes and flavonoids, allows for cessation of viral activities and yet continuation of host cellular activities. Other RNA genome viruses can also be treated using the methods and compositions described herein for HIV. Though not wishing to be bound by any particular theory, it is believed that CKII regulates HIV4 transcription by phosphorylating cellular proteins involved in HIV-1 transactivation containing multiple CKII phosphorylation consensus sequences. Though these two classes of compounds are structurally unrelated, both chrysin and benzothiophene selectively bind to CKII. Furthermore, both chrysin and benzothiophene inhibit human recombinant CKII enzymatic activity and show competitive kinetics with respect to ATP, analogous to the classic CKII inhibitor 5,6-dichloro-1-$\beta$-D-ribofuranosylbenzimidazole (DRB). Moreover, DRB potently inhibits HIV1 expression in chronically infected cells.

Both flavonoids, chrysin in particular, and benzothiophenes act as potent inhibitors of HIV-1 transcription in chronically infected cells (Butera et al, *Mol. Med.* vol. 1, pp. 758–767 (1995); Critchfield et al., *AIDS Res. Hum. Retr.* vol. 12, pp. 39–46) (1996)). They block HIV-1 transcriptional activation in cells treated with tumor necrosis factor-α (TNF-α) or PMA. They also suppress HIV-1 replication in constitutively HIV-1 expressing 8 E5 cells and in OM-10.1 cultures under continued pressure (TNF-α treatment) to express virus. An especially unique feature of these compounds is that the activation and function of NF-κB is not affected. Furthermore, a specificity toward inhibiting HIV-1 transcription is evidenced by the ability of drug-treated cells to not only remain proliferative, but also to retain the capacity to differentiate.

Flavonoids represent a class of compounds of potential use in attenuating HIV activation. These naturally occurring compounds are ubiquitous in vascularized plants and possess a variety of cellular and biochemical effects in animals. For example, certain flavonoids are potent and reversible growth inhibitory agents for numerous human tumor cell lines and also have been found to modify a variety of immune cell responses, including the inhibition of lymphocyte proliferation. Flavonoids also inhibit a large array of mammalian enzymes, including, but not limited to, protein kinase C, cyclic mononucleotide phosphodiesterase, membrane ATPases, cytochrome P-450 enzymes, glutathione S-transferase, cyclooxygenase, and lipoxygenase.

With regard to HIV, some flavonoids have been characterized as inhibiting HIV-1 viral-coded proteins such as reverse transcriptase, protease, and integrase. It is the inventors' surprising finding that flavonoids can be used to inhibit viral replication, particularly HIV, by inhibiting cellular, not viral, proteins. In vitro studies showing inhibition of viral proteins in cultured cells have also shown that the flavonoid baicalin inhibits HIV replication in acutely infected H9 cells, CEM-ss cells, and primary human peripheral blood mononuclear cells (PBMCs). Other work using C81166 cultures indicates that several compounds from the flavan category of flavonoids are effective inhibitors of HIV-1 infection at concentrations where toxicity is very low. More recently, several studies have demonstrated that flavonoids, including chrysin and glycosides of acacetin and apigenin, show significant inhibitory activity in acutely HIV-infected H9 cells. These flavonoids were identified by isolation from particular plant extracts or by the testing of purified compounds.

Two benzothiophene derivative compounds designated PD121871 and PD144795 have been described as inhibiting HIV transcription at micromolar concentrations in models of latent and chronic infection. See S. Butera et al, "Compounds that Target Novel Cellular Components Involved in HIV-1 Transcription." *Molecular Medicine*, Vol. 1 (1995), incorporated herein by reference. These compounds induce a state of viral latency in cells actively expressing HIV, even when maintained under conditions of constant viral stimulation. The compounds selectively inhibited HIV transcription by an unknown mechanism not involving Tat function or NF-κB activation. It was the inventors' present discovery that benzothiophenes could be used to inhibit cellular proteins and thus effect viral replication.

The benzothiophene derivatives were characterized by an ability to block TNF-α-induced HWV activation. However, these agents did not appear to act primarily as TNF antagonists. They did not inhibit NF-κB activation or autocrine TNF-α transcription in response to TNF-α treatment of OM-10.1 cells. Also, they inhibited HIV-1 transcription in chronically infected 8 E5 cells that express HIV-1 independent of exogenous stimulation.

The benzothiophene derivative compounds accelerated the return to viral latency in OM-10.1 cultures when the extracellular stimulus was removed, and induced a state of viral latency in the presence of continued viral stimulation. They also severely restricted viral expression during an acute infection of MT-4 T cells possibly targeting post-integration events.

Cell Lines

Critical tools for studying the efferent phase of the HIV life cycle are the latently infected cell lines such as UI, ACH2, J1, and OM-10.1. The most recently developed of these is the OM-10.1 cell line which displays a rapid down modulation of cell surface CD4 on HIV activation in response to TNF-α, along with the subsequent return of CD4 expression following removal of the HIV-inducing stimulus. HIV activation can also be achieved by phorbol esters such as PMA (phorbol -12-myristate-13-acetate).

The CD4 response is a direct consequence of viral activation and allows a rapid, convenient and highly reproducible assessment of treatments that modify TNF-α expression of HIV from its latent state. In addition, the down modulation of CD4 is not affected by inhibitors of virion assembly or release such as protease inhibitors. Thus, by measuring cell surface CD4 and a virion constituent such as reverse transcriptase (RT), it is possible to discriminate between inhibition of HIV assembly, release and earlier events. For example, in TNF-α-induced OM-10.1 cultures, the protease inhibitor Ro 31-48959 (0.1 μM) completely inhibits RT but has no effect on the down modulation of CD4. In contrast, the antagonist of HIV transactivation, Ro 5-3335, inhibits both of these measures to a similar extent.

Casein Kinase

Human casein kinase II (CKII) is a multifunctional serine/threonine protein kinase whose catalytic subunits α and α' are about 40–44 kD in size, and regulatory subunit β is approximately 29 kD in size. Unlike most serine/threonine kinases, CKII phosphorylates within acidic amino acid stretches. CKII has been proposed as an IκBα kinase, phosphorylating in the motif called the PEST region, in mouse pre-B cells. Multiple proteins which have short half-lives (less than 2 hours) have been shown to contain PEST sequences and to be phosphorylated by CKII. PEST sequences are amino acid sequences that are rich in the amino acids, P (proline), E (glutamic acid), S (serine) and T (threonine).

CKII may also interact with Vpu, an accessory protein encoded by HIV-1. The genome of HIV-1 codes for catalytic and structural proteins as well as for non structural proteins including Vpu. Vpu is present at low concentrations in HIV infected cells, but is absent from virus particles. Vpu is an 81-amino acid amphipathic integral membrane protein with at least two different biological functions: enhancement of virus particle release from the plasma membrane of HIV-1-infected cells, and degradation of the virus receptors CD4. Deletion of the Vpu gene leads to accumulation of viral structural proteins and intracellular budding of premature virus particles, accompanied by an increased cytopathogenicity.

The inventors surprisingly found that viral infections can be treated by specific inhibition of cellular enzymes such as CKII. The role of CKII is demonstrated in that CKII is directly inhibited by two chemically distinct classes of HIV-1 transcriptional inhibitors, the flavonoids and the benzothiophenes. In addition a third chemically distinct compound, the classic CKII inhibitor DRB, also mimics the antiviral properties of the flavonoids and benzothiophenes.

It would not be apparent to those skilled in the art that inhibition of CKII would have any effect on viral infections, because inhibitors of CKII do not effect the activation cycle of viruses such as HIV. Interaction by protein I-κB and Vpu with CKII are known and it is known that these proteins are important for HIV transcription, but surprisingly, inhibition of CKII has no effect on regulation of these proteins Vpu and I-κB.

Further support for the treatment of viral infection by inhibiting CKII while preserving normal host cell functions, is demonstrated by the interaction of CKII with inhibitor-kappa B (I-κB). I-κB undergoes phosphorylation and subsequent degradation in response to activating stimuli (including TNF-α). I-κB degradation results in the release of active nuclear factor-kappa B (NF-κB) that subsequently plays an important role in activating HIV-1 expression. Although some reports indicate that CKII is capable of phosphorylating I-κB on multiple sites, it has been shown that factors that inhibit CKII such as flavonoids and benzothiophenes do not impede either the degradation of I-κB nor the activation and function of NF-κB. Normal degradation of I-κB upon cellular activation is also observed in the presence of DRB.

The Vpu protein of HIV-1 has been shown to be phosphorylated on serine residues 52 and 56 by CKII. These phosphorylations are required for the ability of Vpu to accelerate the decay of CD4. However, Vpu has not been implicated in regulating virus transcription, and viral mutants completely lacking this gene are replication competent.

HIV1 infection is not the only viral infection to be treated by inhibition of CKII because other viruses require cellular CKII to replicate. The most extensively studied of these is vesicular stomatitis virus, the P protein of which must be phosphorylated by CKII to accomplish viral transcription. In addition, CKII is specifically packaged as part of the ribonucleoprotein complex within the vesicular stomatitis virus virion. Other RNA genome viruses also require CKII activity for phosphorylation of the P protein, including respiratory syncitial virus and measles. With regard to retroviruses, cells transformed by Abelson and Moloney murine leukemia viruses contain higher levels of CKII activity.

Compositions contemplated by the present invention include compounds capable of inhibiting CKII. Such compounds are capable of inhibiting CKII in vitro and in vivo and show antiviral activity both in vitro and in vivo. In addition, the compositions of the present invention are capable of inhibiting CKII without detrimentally effecting cellular viability.

Therapeutic induction of viral latency in cells actively expressing HIV would be a new approach to reduce the viral burden and slow disease progression. Therapeutic control of viral transcription in cells expressing HIV constitutes an appealing intervention and a potential supplement to other pharmacologic agents targeting viral-specific gene products. With the identification of relevant molecular targets, these experimental compounds may elucidate new cellular processes that prevent HIV expression and provide a means for prolonging the clinically asymptomatic phase that precedes AIDS.

Treatment of other RNA genome viruses are contemplated by the claimed methods and compositions. Such viruses include, but are not limited to, respiratory syncitial virus, measles virus, and vesicular stomatitis viruses. These viruses, and viruses taxonomically related to these viruses, cause a variety of illnesses in both humans, animals and plants.

Therapeutic Intervention

Compositions for inhibiting protein kinase enzymes such as casein kinase enzymes, can be provided as pharmaceutically acceptable formulations using formulation methods known to those of ordinary skill in the art. These formulations can be administered by standard routes. In general, the combinations may be administered by the topical, transdermal, oral, rectal or parenteral (e.g., intravenous, subcutaneous or intramuscular) route. In addition, the combinations may be incorporated into biodegradable polymers allowing for sustained release of the compound, the polymers being implanted in the vicinity of where drug delivery is desired, for example, at the site of infection.

The dosage of the compound will depend on the condition being treated and the extent of infection, the particular compound, and other clinical factors such as weight and condition of the human or animal and the route of administration of the compound. It is to be understood that the present invention has application for both human and veterinary use. For administration to humans, a dosage of between approximately 5–75 mg/kg/day, preferably , a dosage of between approximately 10–50 mg/kg/day a dosage, most preferably, a dosage of between approximately 10–30 mg/kg/day. Depending on the route of administration, the compound administered and the toxicity of that compound, a preferable dosage would be one that would yield a blood level in the patient of approximately 1–50 $\mu$molar, and more preferably, 1–30 $\mu$molar, and most preferably, 3–10 $\mu$molar.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastiles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having an appropriate particle size, microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood, of course, that the foregoing relates only to preferred embodiments of the present invention and that numerous modifications or alterations may be made therein without departing from the spirit and the scope of the invention as set forth in the Examples and appended claims.

Example I

Characterization and Induction of the OM-10.1 Clone

The OM-10.1 clone was derived by limit diluting the cells which survived an acute HIV-1 infection of HL-60 promyelocytes. After clonal expansion, <10% of OM-10.1 cells were HIV-1+ by direct immunofluorescence and a low level of RT activity was detected in OM-10.1 culture supernatants. By flow cytometric analysis, OM-10.1 cells expressed levels of myeloid-specific surface antigens (CD13, CD14, MY8, CD33, and CD34), HLA-A/B/C, HLA-DR, and CD71 (transferrin receptor) similar to those expressed by the parental uninfected HL-60 cells.

Because of their low constitutive HIV-1 expression, OM-10.1 cultures were treated with either TNF-α or PMA and then evaluated for induced HIV-1 expression. As measured by RT activity of culture supernatants, TNF-α treatment of OM-10.1 cells increased virus expression almost 40-fold while PMA treatment resulted in a 12-fold increase with 36 h. The induction of HIV-1 expression by OM-10.1 cultures was even more dramatic when quantitated by p24 ELISA, in which HIV-1 levels after TNF-α treatment rose 1,000-fold over background in some experiments. Directly associated with the increased HIV-1 expression, virtually 100% of the cells from TNF-α-treated OM10.1 cultures were HIV-1+ by immunofluorescence.

The clonal origin of the OM-10.1 cell line was confirmed by Southern analysis. Total genomic DNA was restricted by Eco RI digestion and probed for the 5' region of the HIV-1 provirus and associated host genomic flank. The DNA from OM-10.1 cells produced a distinct single band of approximately 6.5 kb when analyzed in this manner, whereas no bands were visible from HL-60 DNA. The DNA from 8 E5 cells, a cloned T-cell line harboring a single HIV-1 provirus (Folks et al., *J. Exp. Med.* vol. 164: pp: 280–290 (1986), also produced a single band following hybridization. These results verified the clonal derivation of the OM-10.1 line and established that these cells harbor a single integrated HIV-1 provirus.

Example II

Binding of Proteins to Flavonoids

Affinity Resin.

The affinity resin was made by attachment of 4'-OH-chrysin chrysin (apigenin) to epoxy-activated Sepharose 6B, resulting in chrysin in an ether-linkage. The resin (2 g, dry) was washed with water then 0.1 N NaOH, added to 60 ml 0.01 M apigenin in 0.1 N NaOH (or 0.1 N NaOH only for a non-derivatized control resin), and incubated with gentle mixing for 24 hr at 37° C. The resin then underwent a series of washes (Ghenbot, et al., *Prot. Expr. Purif.* Vol. 3, pp. 470–478 (1992)) and the residual reactive groups capped with 0.1 M ethanolamine for 16 hr at 37° C. After washing with water, the resin was stored at 4° C. in 0.2% $NaN_3$.

Cell Culture and Binding Reactions

OM-10.1 and HL-60 cells as described in Example 1 were propagated in RPMI-1640 supplemented with 10% heat-inactivated fetal calf serum, 2 mM glutamine, and 1% Pen-Strep. Induction of HIV-1 using TNF-α (Butera, S. T., et al, *J. Virol.* Vol. 65, pp. 4645–4653 (1991)), and antiviral assays (Butera, S. T., et al *MoL Med.* Vol. 1, pp. 758–767 (1995), Critchfield, J. W., et al., *AIDS Res. Hum. Retr.* Vol. 12, pp. 39–46 (1996)), were performed as described. For binding studies, cultures were grown to a density of 106 /ml, washed twice with cold PBS, and the cell pellet either flash-frozen in dry ice/ethanol for storage at −70° C., or immediately lysed in 1 ml cold lysis buffer/$10^7$ cells. Lysis buffer consisted of 0.02 M HEPES (pH 7.4), 0.5% Triton X-100, 0.3 M NaCl, 20 mM NaF, 1 mM each of $Na_4 P_2O_7$, $Na_3VO_4$, DTT, EGTA and EDTA, 1 μg/ml each of leupeptin, aprotinin, and pepstatin, 0.5 mM PMSF, and 50 nM okadaic acid. Lysates were incubated on ice for 15 min, centrifuged at 10,000×g for 15 minutes at 4° C., then the supernatants were either used immediately or stored −70° C. For binding reactions with the chrysin affinity resin, lysates (2 ml) were diluted 1:2 with ice-cold 0.02 M HEPES (pH 7.4), then competitor compounds (or 0.1% final DMSO as the control), as indicated, were added to a final concentration of 10 μM and the lysates incubated on ice for 30 min. Chrysin-Sepharose (0.2 ml) was then added and the reactions gently mixed for 1 hr at 4° C. After 3 washes with cold 0.02 M HEPES (pH 7.4), 0.15 M NaCl, 0.25% Triton X-100, bound proteins were eluted with 2 ml 0.02 M ethanolamine (pH 9.5), 0.1% SDS, 0.5 mM chrysin, 1.0% DMSO at 23° C. Samples were concentrated via centrifugation at 23° C. through a 10 kD cut-off membrane (Centricon), then analyzed by SDS-PAGE (8%), and silver stained.

Chemical Analyses and Immunoblotting

Proteins were electrotransferred from the SDS-PAGE gels onto PVDF membrane (BioRad) and stained with either Coomassie Blue (for N-terminal sequencing) or Sulforhodamine B (for MALDI/MS analysis). For N-terminal sequencing, bands were analyzed using a Perkin-Elmer/Applied Biosystems Division 477A Protein Sequencer. Databases used for the matching of sequence data were Swiss Prot.r33, Gen Pept.r97, and Owl.r28.2.

For MALDI/MS analysis (Sutton, C. W., et al, *Electrophoresis* Vol. 16, pp. 308–316 (1995)), bands were digested with 8 μl 50 mM ammonium bicarbonate containing 1% (w:v) octylglucoside and 40 μg/μl trypsin. Samples were incubated for 16 hr at 23° C., dried in a Speed Vac and resuspended in 10 μl formic acid/ethanol (1:1). Aliquots (0.5/μl) were applied to the MALDI/MS sample slide and mixed with an equal volume of MALDI/NIS matrix solution (α-cyano-4-hydroxycinnamic acid in acetonitrile/TFA (1:1)). Mass spectra were acquired on a Voyager RP mass spectrometer (Perseptive Biosystem). Oxidized bovine insulin B chain (MH+ 3496.9) was used as an internal standard for mass calibration. Sample masses obtained were used to perform a peptide-mass search using the program MS-Fit (internet version http://rafael.ucsf.edu/MS-Fit.html).

For Western analysis, proteins were transferred to PVDF and probed with a combination of two antibody reagents, one recognizing an epitope common to both the α and α' subunit of CKII (Upstate Biotechnology) and the other reacting with the β subunit of CKII (a gift from D. Litchfield, University of Western Ontario). Final detection was with enhanced chemiluminescence (Amersham).

Enzyme Kinetics

Measurement of human recombinant CKII (ααββ form, Boehringer-Manheim) activity was by a modification of a published procedure (Marshak D. R., et al. *Methods Enzymol.* Vol. 200, pp. 134–156 (1991)). Reactions were carried out at 37° C. in 0.025 M HEPES (pH 7.4), 0.15 M KCl, 0.01 M $MgCl_2$, 1.4 mM β-mercaptoethanol, 1 mM DTT, 1 mM EGTA, 10% glycerol, 0.32 mM synthetic CKII peptide, (RRRDDDSDDD), 1 μU/μl CKII, and the indicated concentrations of ATP and test agents. Unincorporated [$\gamma$-$^{32}$P] ATP was removed by spotting reactions onto P81 phosphocellulose paper (Whatman) and washing in 0.75 mM phosphoric acid then acetone.

Four Proteins Bound Selectively HIV-1 Inhibitory Flavonoids.

To identify the targets of HIV-1 inhibitory flavonoids, Sepharose was derivatized with the flavonoid chrysin and interacted with lysates from OM-10.1 cells as described in Example I. Cultures induced to maximally express HIV-1 (24 hr treatment with TNF-α) were utilized to ensure the presence of both cellular and viral proteins. SDS-PAGE and silver staining of bound proteins revealed multiple proteins associating with the chrysin-resin, while a negative control resin (not derivatized) showed negligible protein binding. When free chrysin or a second HIV-inhibitory flavonoid, apigenin, was added to the lysate as a competitor prior to interaction with the chrysin-resin, four proteins (p44, p40, p29, p28) were specifically inhibited in their binding to the resin. In contrast, the addition of two flavonoids lacking HIV-1 inhibitory activity in OM 10.1 system, catechin and hesperidin, had no effect on the binding profile.

Chrysin-binding Proteins p44, p40, p29, & p28 were Constitutively Expressed Cellular Products To establish whether the 4 chrysin-binding proteins were present only in cells maximally producing virus, lysates were prepared from uninduced OM-10.1 cells or OM-10.1 cells induced to produce variable amounts of HIV-1 by adjusting the exposure time to TNF-α (Butera, et al. (1991)). Using the addition of free chrysin as a competitor to discern specific binding, similar amounts of the same 4 chrysin-binding proteins (p44, p40, p29, & p28) were detected by gel electrophoresis regardless of the level of virus expression. These same 4 proteins were also identified in lysates of HL-60 cells, the uninfected parental line of OM-10.1, further indicating that these proteins were of cellular origin.

Chemical, Immunologic and Specific Inhibitor Methods Indicated that 3 of the 4 Chrysin-binding Proteins were the Subunits of CKII.

The 4 chrysin-binding proteins were excised after transfer to PVDF and subjected to N-terminal amino acid sequence analysis. Sequence information was not obtainable from p44 and p29, possibly due to blockage of the N-terminus. However, 14 N-terminal residues were identified for p40, and this sequence was identical to the N-terminal sequence of the α' subunit of human CKII (a 40 kD protein). Further analysis of p29 by matrix-assisted laser desorption ionization mass spectrometry yielded a tryptic peptide profile that best matched the β subunit of CKII (a 29 kD protein). Thus, p40 and p29 were identified as the α' and β subunits of CKII, respectively. Furthermore, CKII is a heterotetrameric enzyme (≈130 kD) containing, in addition to α' and β subunits, an α subunit of 44 kD, a mass identical a third chrysin-binding protein for which chemical analysis was not pursued beyond attempted sequencing.

To further confirm that the chrysin-binding proteins were indeed the subunits of CKII, resin-binding reactions were performed using a selective inhibitor of CKII activity, 5,6 dichloro-1-β-D-ribofuranosylbenzimidazole (DRB), and the results analyzed by silver staining and anti-CKII immunoblotting. By silver staining, the addition of DRB to the lysate prevented the binding of the same proteins that were competed by free chrysin, the only exception being p28. By parallel immunoblot analysis, the α, α' and β subunits of CKII bound to the chrysin resin, migrated in accordance with p44, p40, and p29 as observed in silver staining, and the addition of either free chrysin or DRB eliminated their immunodetection. Since the apparent mass of the β chain of CKII is increased by phosphorylation (Luscher, B. L., et al. *Eur. J. Biochem.* Vol. 220, pp. 521–526 (1994)), it was possible that p28 represented an unphosphorylated form of p29. However, when the proteins eluted from the chrysin resin were treated with alkaline phosphatase prior to electrophoresis, the increased mobility of p29 remained distinct from p28, suggesting that p28 was not related to the β subunit of CKII. Furthermore, the major p28 band observed by silver stain was absent by immunoblot analysis. This absence was not due to an inability of the CKIIβ antibody to recognize dephosphorylated CKIIβ, which had lower apparent mass following alkaline phosphatase treatment. Thus, chemical, immunologic, and specific inhibitor methods indicated that 3 of the 4 chrysin-binding proteins are the subunits of CKII.

To determine that CKII is also the target of the benzothiophenes, benzothiophenes were tested in the resin binding assay. Competition by an HIV-inhibitory benzothiophene, PD 144795, resulted in a pattern of binding inhibition identical to that of DRB, while a non-HIV inhibitory analog, PD 132486, had no effect. Like DRB, PD 144795 did not alter the binding of p28 to chrysin, implying that this specific chrysin-binding protein may be unrelated to the antiviral properties of these compounds.

The CKII Inhibitor DRB blocked HIV-1 Expression in Activated Cells.

Figure 2:
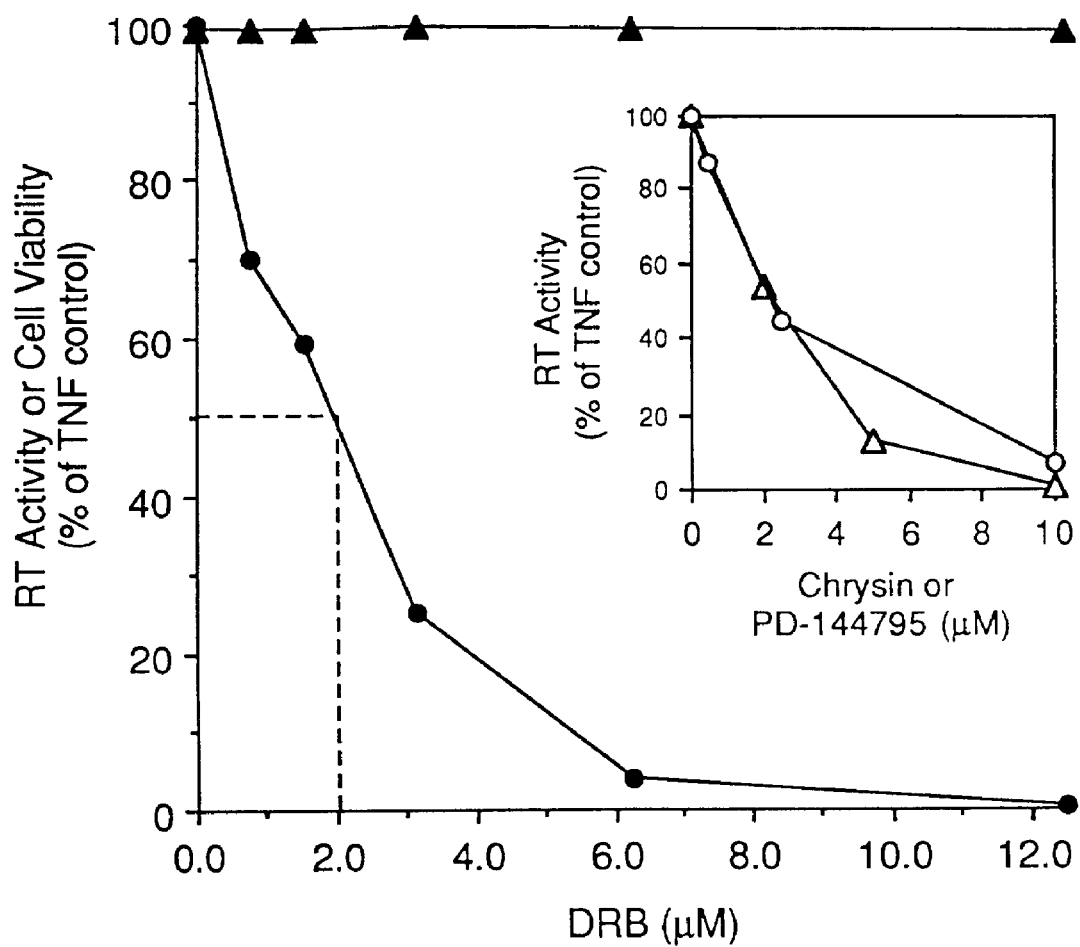
FIG. 2 is a graph showing the inhibition of HIV-1 expression and toxicity in OM-10.1 cells by DRB, and similarity to inhibition imposed by chrysin and PD 144795. Reverse transcriptase activity (—✕—) was measured (as taught in Butera et al, *Mol. Med.* vol. 1, pp. 758–767 (1995)) in culture supernatants 48 hr after HIV activation, and cell viability (—▲—) was assessed at 24 hr by flow cytometric analysis of propidium iodide exclusion. Inset: A graph showing the inhibition of HIV-1 expression in OM-10.1 cells by chrysin- (—△—) and PD 144795 (—☆—) treatment of HIV-1.

HIV-1 activation experiments were conducted in the presence or absence of DRB. DRB treatment markedly inhibited HIV-1 expression in TNF-α-treated OM-10.1 cultures, as shown by a reduction in culture supernatant reverse transcriptase activity ($ED_{50}$≈2 μM). Culture viability did not decline over the effective dose range of DRB, indicating that the inhibition of HIV-1 expression was not a non-specific toxicity effect. The pattern of HIV-1 inhibition by DRB was remarkably similar to that previously observed with the flavonoids and benzothiophenes in that NF-κB activation and function appeared normal and there was no requirement for pretreatment with compound relative to the addition of TNF-α. Furthermore, the effective dose range of DRB (1–10 μM) was nearly identical to that of the other compounds (FIG. 2, inset), and toxicity over the effective dose range for the other compounds was also negligible. While DRB has been shown to be quite specific toward inhibiting CKII, this compound does display appreciable inhibitory activity against casein kinase I (Shugar, D. *Cell. Mol. Biol. Res.* Vol. 40, pp. 411–419 (1994)). However, in the OM-10.1 induction system, a more selective inhibitor of casein kinase I (CKI-7) was without HIV-1 inhibitory activity.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of treating measles virus infection in a human or animal in need thereof, comprising administering to the human or animal an effective amount of a composition comprising a compound selected from the group consisting of flavonoids, benzothiophenes, and 5,6-dichloro-1-β-D-ribofuranosylbenzinidazole (DRB), and their precursors, analogs, metabolites and hydrolysis products, wherein casein kinase II is inhibited.

2. The method of claim 1, wherein the composition comprises a flavonoid.

3. The method of claim 1, wherein the composition comprises a benzothiophene.

4. The method of claim 1, wherein the compositions comprises 5,6-dichloro-1-β-D-ribofuranosylbenzimidazole (DRB).

5. A method of treating respiratory syncytial virus infection in a human or animal in need thereof, comprising administering to the human or animal, an effective amount of a composition comprising a compound selected from the group consisting of flavonoids, benzothiophenes, and 5,6-dichloro-1-β-D-ribofuranosylbenzimidazole (DRB), and their precursors, analogs, metabolites and hydrolysis products, wherein casein kinase II is inhibited.

6. The method of claim 5, wherein the composition comprises a flavonoid.

7. The method of claim 5, wherein the composition comprises a benzothiophene.

8. The method of claim 5, wherein the composition comprises 5,6-dichloro-1-β-D-ribofuranosylbenzimidazole (DRB).

* * * * *